(12) United States Patent
Inoue (10) Patent No.: US 9,134,176 B2
(45) Date of Patent: Sep. 15, 2015

(54) DEVICE FOR ACQUIRING OPTICAL INFORMATION OF OBJECT

(71) Applicant: CANON KABUSHIKI KAISHA, Tokyo (JP)

(72) Inventor: Yukihiro Inoue, Tama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/450,026

(22) Filed: Aug. 1, 2014

(65) Prior Publication Data

US 2015/0042989 A1 Feb. 12, 2015

(30) Foreign Application Priority Data

Aug. 6, 2013 (JP) .................................. 2013-163364

(51) Int. Cl.
*G01J 3/44* (2006.01)
*G01J 3/02* (2006.01)
*G01N 21/65* (2006.01)

(52) U.S. Cl.
CPC ................. *G01J 3/0218* (2013.01); *G01J 3/44* (2013.01); *G01N 21/658* (2013.01); *G01N 2021/653* (2013.01)

(58) Field of Classification Search
CPC .............. G01J 3/02; G01J 3/44; G01N 21/65; G01N 21/658; G01N 2021/656
USPC .................................................. 356/300–334
See application file for complete search history.

(56) References Cited

U.S. PATENT DOCUMENTS

2011/0075142 A1* 3/2011 Maity et al. ................... 356/326

FOREIGN PATENT DOCUMENTS

JP 2011-180504 A 9/2011

OTHER PUBLICATIONS

Martin, et al., "Alignment-free, all-spliced fiber laser source for CARS microscopy based on four-wave-mixing", Optics Express, vol. 20, No. 19, pp. 21010-21018, Sep. 10, 2012.

* cited by examiner

*Primary Examiner* — Abdullahi Nur
(74) *Attorney, Agent, or Firm* — Canon USA Inc. IP Division (57) ABSTRACT

An information acquiring device that acquires information on a measurement object includes: a dividing section that divides pulsed light having a center wavelength λc emitted from a light source into lights for a plurality of optical paths; waveguides provided in each of the optical paths; a multiplexing section that multiplexes lights emitted from the waveguides; and an information acquiring section that acquires information through detection of a light obtained by the multiplexing by the multiplexing section and applied to the object. In the information acquiring device, the waveguides provided in the optical paths, respectively are waveguides having different zero dispersion wavelengths, and the waveguides generate a plurality of wavelength-converted lights each having a center wavelength different from the center wavelength λc of the pulse light.

14 Claims, 5 Drawing Sheets

FIG. 3A    β2 > 0 and β4 > 0

FIG. 3B    β2 > 0 and β4 < 0

FIG. 3C    β2 < 0 and β4 > 0

FIG. 3D    β2 < 0 and β4 < 0

DEVICE FOR ACQUIRING OPTICAL INFORMATION OF OBJECT

BACKGROUND OF THE INVENTION

1. Field of the Invention

The present invention relates to information acquiring devices, and in particular relates to an information acquiring device using a plurality of pulse lights with different center wavelengths.

2. Description of the Related Art

Various kinds of information can be obtained on a measurement object in a manner such that the object is irradiated with a pulse light and a light reflected or scattered by the object, a light passing through the object, or a light emitted from the object is detected for acquiring information.

In recent years, material identification has been an active area of research, which is conducted by irradiating a measurement object with pulses of light (pulse lights) with different center wavelengths and two variable different wavelengths, detecting lights generated by the object based on stimulated Raman scattering (SRS) or coherent anti-stokes Raman scattering (CARS), and obtaining a Raman spectrum. The stimulated Raman scattering and the coherent anti-stokes Raman scattering are hereinafter simply referred to as SRS and CARS, respectively, in some cases.

Optics Express, Vol. 20, No. 19, pp. 21010-21018, Sep. 10, 2012 (hereinafter referred to as Non-Patent Document 1) discloses a method of guiding a pulse light with a specific wavelength into a photonic crystal fiber having normal dispersion at the wavelength of the pulse light, thereby generating a wavelength-converted light with a narrow spectral bandwidth; and carrying out CARS imaging using the pulse lights with two different wavelengths corresponding to the wavelengths before and after the wavelength conversion.

Further, Japanese Patent Application Laid-Open No. 2011-180504 (hereinafter referred to as Patent Literature 1) discloses a method of guiding a pulse light with a specific wavelength into a plurality of photonic crystal fibers having anomalous dispersion at the wavelength of the pulse light, thereby generating a wavelength-converted light with a wide spectral bandwidth; and carrying out CARS imaging using the pulse lights with two different wavelengths corresponding to the wavelengths before and after the wavelength conversion.

However, there are shortcomings with the existing techniques described above. Specifically, the method disclosed in Non-Patent Literature 1 is disadvantageous in that since the wavelength of a light source is only variable in a small range, a CARS signal generated in a biological tissue has a small range of frequency.

Moreover, it is also disadvantageous in that since the output of the light source has a large noise component, the ratio of the noise to the CARS signal (signal-to-noise ratio) decreases.

In the meanwhile, the method disclosed in Patent Literature 1 is disadvantageous as well in that using photonic crystal fibers having anomalous dispersion (group velocity dispersion β2<0) causes that the spectral bandwidth after wavelength conversion is so wide that the utilization efficiency of the pulsed light used in CARS imaging is reduced.

Moreover, the method disclosed in Patent Literature 1 causes that the output of the light source has a large noise component and this reduces the signal-to-noise ratio.

SUMMARY OF THE INVENTION

An object of the present invention is therefore to provide an information acquiring device that uses a pulsed light with high utilization efficiency and an increased wavelength variable range.

An information acquiring device according to one embodiment acquires information on a measurement object by irradiating the object with a pulsed light emitted from a light source and detecting a light reflected or scattered by the object, a light passing through the object, or a light emitted from the object. The information acquiring device includes: a dividing section configured to divide pulsed light having a center wavelength λc emitted from the light source section into lights for a plurality of optical paths; waveguides provided in each of the optical paths; a multiplexing section configured to multiplex lights emitted from the waveguides; and an information acquiring section configured to detect a light generated by irradiating the object with the lights multiplexed by the multiplexing section. In the information acquiring device, the waveguides provided in the optical paths are waveguides having different zero dispersion wavelengths, the waveguides generate a plurality of wavelength-converted lights each having a center wavelength different from the center wavelength λc of the pulse light, and the waveguides satisfy the relations of $\beta_2 > 0$ and $\beta_4 < 0$ at the center wavelength of λc where $\beta_2$ is the group velocity dispersion for the waveguides and $\beta_4$ is a second derivative of the group velocity dispersion $\beta_2$.

Further features of the present invention will become apparent from the following description of exemplary embodiments with reference to the attached drawings.

DESCRIPTION OF THE EMBODIMENTS

Figure 1A:
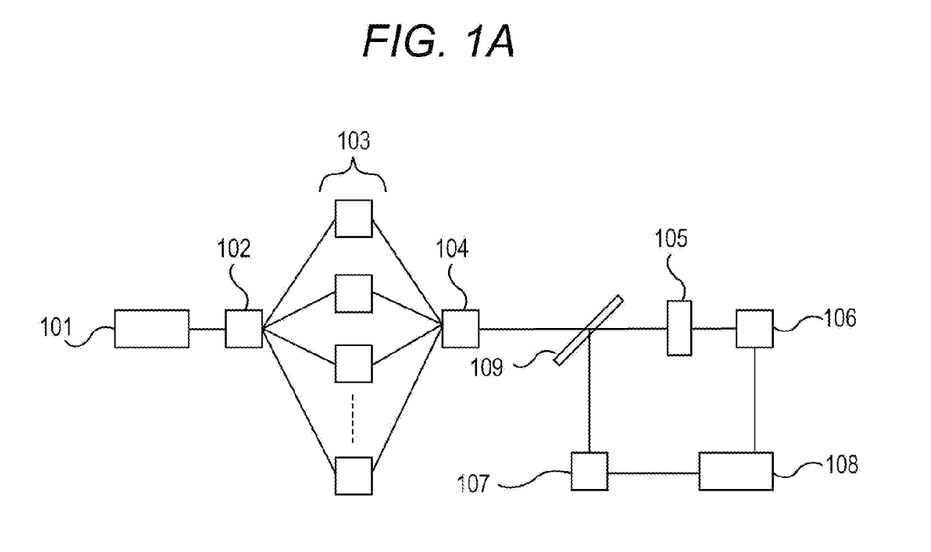
FIG. 1A is a schematic drawing illustrating an exemplary configuration of an information acquiring device according to an embodiment.
Figure 1B:
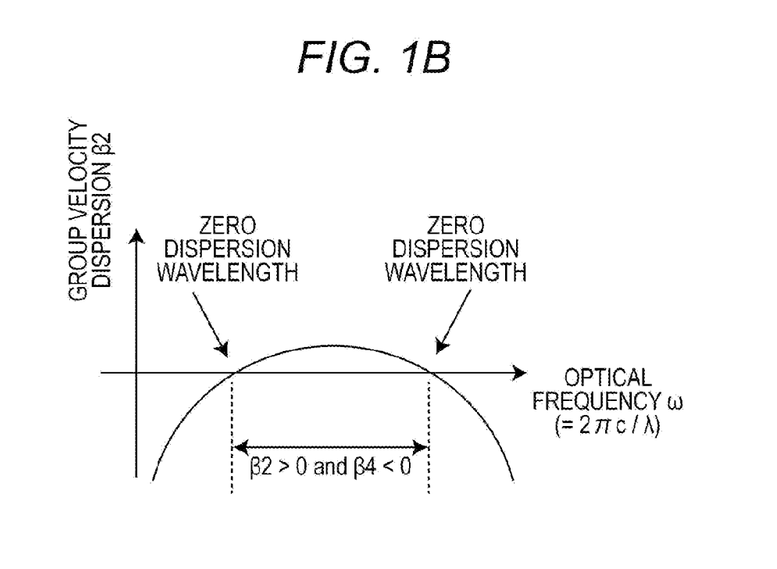
FIG. 1B is a Cartesian graph illustrating an example of the group velocity dispersion characteristics of waveguides according to the embodiment.

An example of a configuration of an information acquiring device according to an embodiment of the present invention will be described below with reference to the drawings. It is to be noted that the present invention is not particularly limited to the configuration of the embodiment described below. FIG. 1A is a schematic drawing illustrating an information acquiring device according to the embodiment, and FIG. 1B is a graph illustrating an example of the group velocity dispersion characteristics of waveguides according to the embodiment.

The information acquiring device according to the embodiment is configured so as to acquire information on a measurement object (the object) by irradiating the object with a pulse light emitted from a light source and detecting a light reflected or scattered by the object, a light passing through the object, or a light emitted from the object.

Specifically, as FIG. 1A illustrates, the information acquiring device includes: a light source 101 that emits a pulse light with a center wavelength of λc; a dividing section 102 that divides the pulse light emitted from the light source 101 into lights for a plurality of optical paths; and a plurality of waveguides 103 provided in each of the optical paths, having different zero dispersion wavelengths.

The information acquiring device further includes a multiplexing section 104 that multiplexes lights output from the waveguides 103; light detecting sections 106 and 107 that detect a light generated by applying a light output from the multiplexing section 104, to the object; and an information acquiring section 108 that acquires information on the object 105 based on the intensities of the lights detected by the light detecting sections 106 and 107. The light detecting section 106 mainly detects lights travelling in a direction from the measurement object 105 to the light detecting section 106, such as lights having passed through the object 105. The light detecting section 107 mainly detects lights which are reflected or scattered by the object 105 and are subsequently reflected to the light detecting section 107 by a half mirror 109.

That is, the light detecting sections 106 and 107 are provided for the purpose of detecting all of the lights generated for various reasons. Any light generated is detected by the light detecting sections 106 and 107 regardless of the reasons for the generation. More than two light detecting sections (106 and 107) may be provided.

A light generated by applying a light emitted from the light source 101 to the object 105 includes a portion of the applied light which is reflected or scattered by the object 105, or passing through the object 105 without being absorbed into the object 105.

Further, a light generated by applying the light emitted from the light source 101 to the object 105 includes fluorescence, phosphorescence, etc. generated by absorption of the light applied to the object 105, in a case where the object 105 contains fluorescent material, for example.

Examples of a light generated by applying the light emitted from the light source 101 to the object 105 include multiphoton excitation fluorescence, high-order harmonic waves generated by non-linear effects, and lights resulting from phenomena such as stimulated Raman scattering and coherent anti-stokes Raman scattering.

The absorption mentioned above includes an absorption based on difference in usual scattering angles, an absorption by electron excitation, an absorption by molecular vibration, and a multiphoton absorption thereof.

A half mirror 109 may be provided on an optical path of a light travelling from the light source 101 to the object 105 for easy detection of a light reflected or scattered by the object 105, as illustrated in the drawing.

Since the object 105 has optical characteristics varying, depending on the materials of the object 105 or the material compositions of the object 105, for example, the light detecting section 106 detects lights generated from the object 105, such as reflected light, scattered light, passing-through light, fluorescence, and phosphorescence. Further, information on the optical characteristics of the object 105 can be obtained by calculating a variation in the intensity of the light detected by the light detecting section 106 with respect to the intensity of the light applied to the object 105. In addition, information on the materials of the object 105 or the material compositions, for example, can be obtained in some cases from the information on the optical characteristics.

All that the light detecting section 106 needs to detect is at least one of reflected light, scattered light, passing-through light, fluorescence, and phosphorescence.

Since the multiplexing section 104 outputs a light formed by multiplexing a plurality of pulse lights having different center wavelengths, information on the optical characteristics of the object 105 for the different wavelengths can be concurrently acquired.

Moreover, as the waveguides 103, waveguides with normal dispersion at the wavelength of an incoming pulse light, in other words, waveguides with positive group velocity dispersion are used.

Figure 3A:
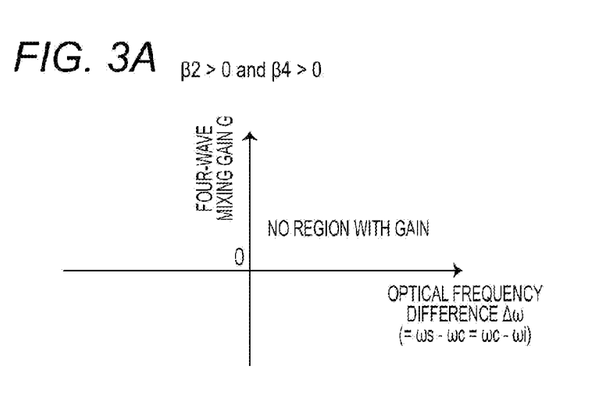
FIGS. 3A, 3B, 3C and 3D are Cartesian graphs illustrating principles of wavelength conversion by four-wave mixing according to another embodiment.
Figure 3B:
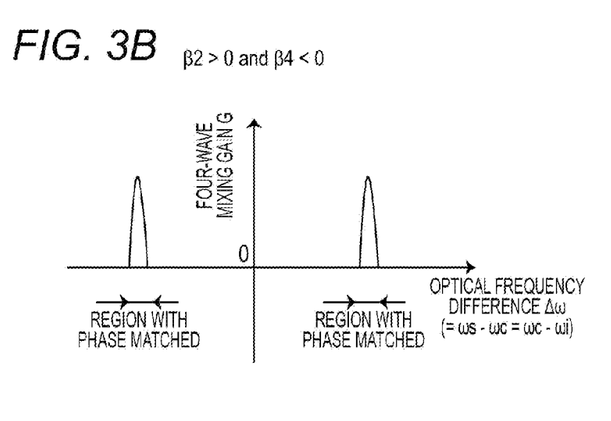

In the embodiment, the waveguides 103 need to satisfy the relations of $\beta_2 > 0$ and $\beta_4 < 0$ where the group velocity dispersion for the waveguides 103 at the wavelength of the incoming light is denoted by $\beta_2$ and a second derivative of the group velocity dispersion $\beta_2$ is denoted by $\beta_4$. When the waveguides 103 have wavelength dispersion satisfying the relations of $\beta_2 > 0$ and $\beta_4 < 0$, pulse lights going through the waveguides 103 have a narrow spectral bandwidth as FIG. 3B illustrates. Hence, most of the respective lights having gone through the waveguides 103 can be used for SRS or CARS. This means that high utilization efficiency of the pulse lights is achieved.

Figure 3C:
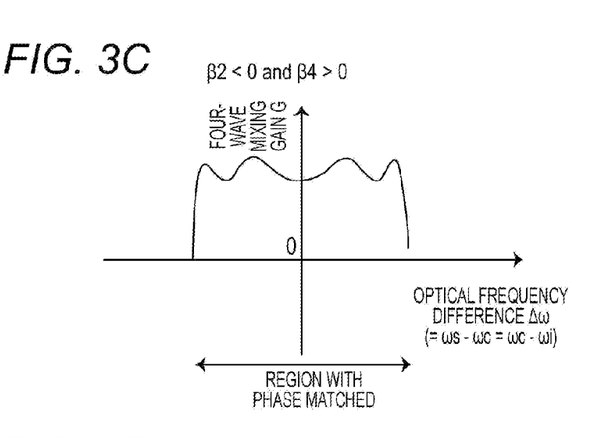
Figure 3D:
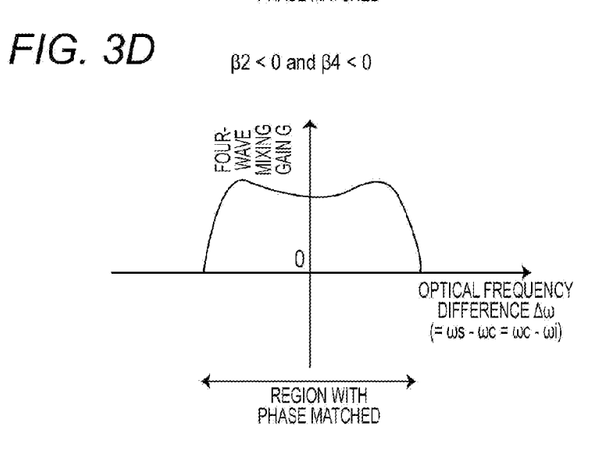

On the other hand, when a waveguide has anomalous dispersion ($\beta_2 < 0$) as described in Patent Literature 1, a pulse light going through the waveguide has a large spectral bandwidth as FIG. 3C and FIG. 3D illustrate. Hence, only part of pulse lights with a large spectral bandwidth can be used for SARS or CARS. This means that utilization efficiency of the pulse lights is low.

Details of the embodiment will be described below.

FIG. 1B is a graph plotting the characteristics of the group velocity dispersion $\beta_2$ of the waveguides 103 against the optical frequency.

When the relation of $\beta_4 < 0$ is satisfied, the graph of FIG. 1B is in the shape of a convex along the vertical axis.

The relation can be satisfied by adjusting the shapes of the waveguides according to the material of the waveguides 103.

For example, when optical fibers are used for the waveguides 103, the relation can be satisfied by adjusting the waveguide dispersion.

Setting all the waveguides 103 as described above makes it possible to generate pulse lights with narrow spectral bandwidths and converted wavelengths, at wavelengths far by $\pm\Delta\lambda$ with respect to the wavelength of the incoming pulse light. For the wavelength conversion, four-wave mixing, which is a third-order non-linear phenomenon, is used.

Next, the principle of the wavelength conversion by four-wave mixing will be described.

The four-wave mixing is a third-order non-linear phenomenon of the interaction among four lights with different wavelengths making energies of two light of the four lights change into energies of the other two lights.

For example, when lights with frequencies of $\omega_1$ and $\omega_2$ are drawn into the waveguides 103, lights with frequencies of $\omega_3$ and $\omega_4$ are newly generated, the frequencies $\omega_3$ and $\omega_4$ satisfying the relation of $\omega_1 + \omega_2 = \omega_3 + \omega_4$.

Further, when an incoming light has a single frequency of $\omega_c$ and the relation of $\omega_c = \omega_1 = \omega_2$ is established, lights are newly generated at the wavelengths symmetrically shifted from the frequency of $\omega_c$ approximately by frequency differences of $\pm\Delta\omega$.

A higher frequency light and a lower frequency light are generally called a signal light and an idler light, respectively. The frequency of the signal light, $\omega_s$ is expressed as $\omega_c + \Delta\omega$, and the frequency of the idler light, $\omega_i$ is expressed as $\omega_c - \Delta\omega$.

Moreover, when the respective propagation constants of the incoming pulse light drawn into the waveguides 103, the signal light, and the idler light are denoted by $\beta_c$, $\beta_s$, and $\beta_i$, the constants need to satisfy the phase matching condition expressed by the following formula (1).

$$-4\gamma P_0 < \Delta\beta = \beta_s + \beta_i - 2\beta_c < 0 \gamma = \frac{\omega_c}{c}\frac{n_2}{A_{\textit{eff}}} \quad \text{Formula (1)}$$

$\Delta\beta$, $\gamma$, P0, n2, Aeff, and c in the formula denote a mismatching among the propagation constants of the lights in the waveguides 103, a non-linear coefficient of the waveguides 103, a peak intensity of the incoming pulse light, a non-linear refractive index, an effective cross section, and a velocity of light, respectively. The signal light and the idler light are generated with excellent efficiency when the phase matching condition is satisfied.

Subsequently, the mismatching $\Delta\beta$ among the propagation constants of the lights in the waveguides 103 can be expressed by the following formula (2) using the frequency difference $\Delta\omega$.

$$\Delta\beta = \beta_2(\Delta\omega)^2 + \beta_4(\Delta\omega)^4/12 \quad \text{Formula (2)}$$

$\beta 2$ and $\beta 4$ in the formula denote group velocity dispersion for the incoming pulse light drawn into the waveguides 103, and a second derivative of the group velocity dispersion $\beta 2$, respectively. The group velocity dispersion $\beta$2 is a second derivative of the propagation constant $\beta c$ of the incoming pulse light.

Further, a gain G obtained by four-wave mixing in this case is expressed by the following formula (3).

$$G = \left| \frac{\sinh\left(\sqrt{1-(1+\Delta\beta/2\gamma P_0)^2}\gamma P_0 L\right)}{1-(1+\Delta\beta/2\gamma P_0)^2} \right|^2 \quad \text{Formula (3)}$$

L in the formula denotes the length of each waveguide 103.

The graphs representing Formula (2) and Formula (3) are illustrated in FIGS. 2A, 2B, 2C and 2D and FIGS. 3A, 3B, 3C and 3D, respectively.

The vertical axis and horizontal axis in FIGS. 2A, 2B, 2C and 2D represent $\Delta\beta$ and $\Delta\omega$, respectively, and the vertical axis and horizontal axis in FIGS. 3A, 3B, 3C and 3D represent G and $\Delta\omega$, respectively.

Four types of graphs are illustrated in FIGS. 2A, 2B, 2C and 2D, and in FIGS. 3A, 3B, 3C and 3D; these figures illustrate the cases where $\beta 2$ and $\beta 4$ have negative and positive values.

Moreover, FIGS. 2A-2D additionally illustrate a range in which the phase matching condition expressed by Formula (1) holds. According to Formula (1), since the values of the non-linear coefficient $\gamma$ of the waveguides 103 and the peak intensity $P_0$ of the incoming pulse light are both positive, $\Delta\beta$ has a negative value.

Figure 2A:
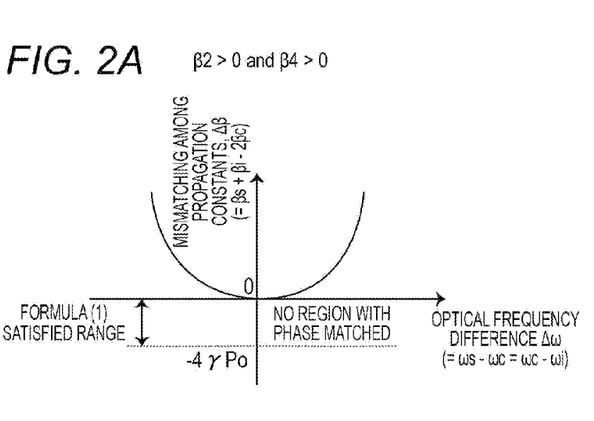
FIGS. 2A, 2B, 2C and 2D are Cartesian graphs illustrating principles of wavelength conversion by four-wave mixing according to an embodiment.
Figure 2B:
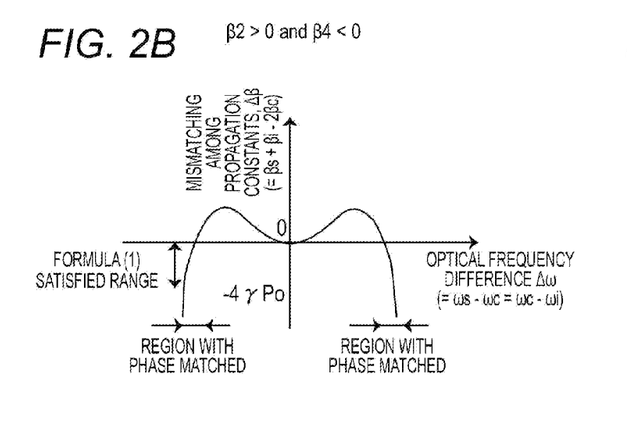
Figure 2C:
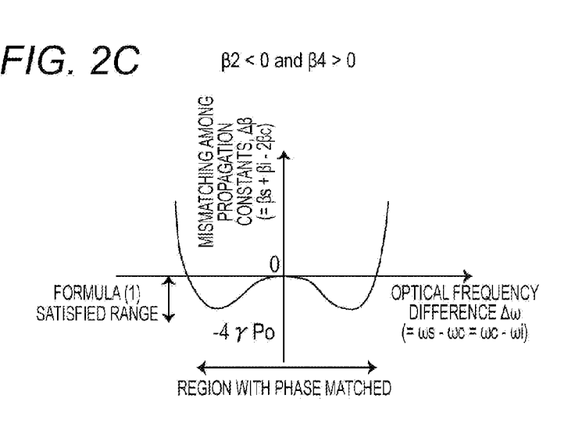
Figure 2D:
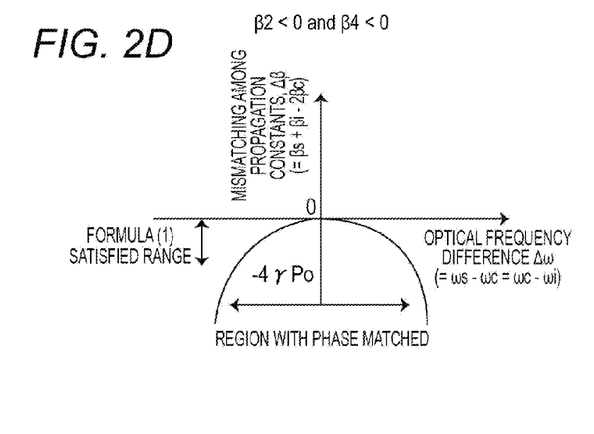

Hence, as FIGS. 2C and 2D illustrate, when the incoming pulse light has a wavelength in an anomalous dispersion region where $\beta 2$ is smaller than 0, the range of $\Delta\omega$ satisfying the phase matching condition expressed by Formula (1) is relatively wide.

In other words, as FIGS. 3C and 3D illustrate, when a pulse light with such a frequency is drawn into the waveguides 103, four-wave mixing gain G exists in a relatively wide frequency bandwidth and a signal light and an idler light are generated having large spectral bandwidths. On the other hand, in the present invention, the incoming pulse light is operated in a normal dispersion region where $\beta 2$ is larger than 0 and $\beta 4$ is smaller than 0, as FIG. 2B illustrates.

In this time, $\Delta\omega$ satisfying the phase matching condition expressed by Formula (1) exists in a relatively narrow spectral region at a wavelength away from the frequency of the incoming pulse light.

In other words, as FIG. 3B illustrates, when a pulse light with a specific frequency is drawn into the waveguides 103, the four-wave mixing gain G exists in a relatively narrow frequency bandwidth and a signal light and an idler light are generated in a narrow frequency bandwidth.

A frequency shift $\Delta\omega$ (wavelength shift $\Delta\lambda$) of the signal light and the idler light from the frequency (the wavelength) of the incoming pulse light, and a frequency bandwidth $\delta\omega$ (wavelength bandwidth $\delta\lambda$) of the signal light and the idler light are determined by the following formula (7) from the following formula (4).

$$\Delta\omega = \sqrt{\frac{12\beta_2}{|\beta_4|}} = \sqrt{\frac{12\beta_3(\omega_c - \omega_0)}{|\beta_4|}} \quad \text{Formula (4)}$$

$$\Delta\lambda = \frac{1}{A}\sqrt{\frac{12\beta_2}{|\beta_4|}} = \frac{1}{A}\sqrt{\frac{12\beta_3 A(\lambda_0 - \lambda_c)}{|\beta_4|}} \quad A = \frac{2\pi c}{\lambda_0^2} \quad \text{Formula (5)}$$

$$\delta\omega = \frac{24\gamma P_0}{|\beta_4|\Delta\omega^3} \quad \text{Formula (6)}$$

$$\delta\lambda = \frac{24\gamma P_0}{A^4|\beta_4|\Delta\lambda^3} \quad \text{Formula (7)}$$

In the formulas above, $\lambda c$ denotes a center wavelength of the incoming pulse light, $\lambda 0$ denotes a zero dispersion wavelength of the waveguides 103, and $\beta 3$ denotes a primary derivative of the group velocity dispersion $\beta 2$ at the zero dispersion wavelength.

Formula (5) shows that the wavelength shift $\Delta\lambda$ increases as the difference between the wavelength of the incoming pulse light and the zero dispersion wavelength of the waveguides 103 increases.

Therefore, it is possible to generate a plurality of wavelength-converted lights with different center wavelengths apart from the wavelength of the incoming pulse light, by using a plurality of waveguides 103 with different zero dispersion wavelengths.

Additionally, changing the center wavelength $\lambda c$ of the incoming pulse light can further shift the wavelengths of the plurality of wavelength-converted lights.

Using the plurality of wavelength-converted lights as described above can further extend the wavelength variable range. Further, Formula (7) indicates that using waveguides with a small non-linear coefficient $\gamma$ and a large $\beta 4$ enables generation of wavelength-converted lights with a narrow spectral bandwidth $\delta\lambda$.

Furthermore, because four-wave mixing is a third-order non-linear phenomenon, the wavelength conversion efficiency varies in proportion to the intensity of the incoming pulse light.

Specifically, the intensity after wavelength conversion is in proportion to the square of the intensity of the incoming pulse light. Hence, a low-intensity light has low (or reduced) conversion efficiency, and a high-intensity light is efficiently converted in wavelength.

Even if a noise component such as spontaneous emission light has been superimposed on the incoming pulse light, the wavelength-converted lights have only small amounts of noise components since a low-intensity noise component has an extremely low conversion efficiency.

The intensities of The signal component and the noise component of the incoming light pulse are denoted by Is and In, respectively, and the intensities of the signal component and the noise component after wavelength conversion are denoted by Is' and In', respectively.

The signal component after wavelength conversion, Is' is expressed by $k \times Is^2$ (k is a constant of proportion), and the noise component after wavelength conversion, In' is expressed by $k \times In^2$.

Since the signal-to-noise ratio for the incoming pulse light and the signal-to-noise ratio after wavelength conversion are indicated by Is/In and Is'/In'=$(Is/In)^2$, respectively, the signal-to-noise ratio after wavelength conversion equals to the square of the signal-to-noise ratio of the incoming light pulse, and is thus larger than the signal-to-noise ratio of the incoming light pulse.

In this way, using the wavelength-converted lights alone in information acquisition can provide an excellent signal-to-noise ratio. In the embodiment, the wavelength variable range of the pulse light can be extended in a manner that a plurality of waveguides with different zero dispersion wavelengths are used for generation of a plurality of wavelength-converted lights.

In addition, since the wavelength-converted lights have small amounts of noise components, using the wavelength-converted lights alone in information acquisition can provide an excellent signal-to-noise ratio.

Next, the light source will be described.

Although the light source according to the embodiment is not particularly limited as long as it emits a pulse light, a wavelength variable light source is desirable that can change the wavelength of a light to be emitted.

A pulse light emitted from the light source according to the embodiment preferably has a pulse width of 1 ns or smaller, and more preferably has a width of 100 ps or smaller.

The reason for this is that as the pulse light has a narrower pulse width, it has a larger peak intensity and the presence or absence of non-linear effects of the measurement object can be more easily found. Further, the pulse width is preferably 1 ps or larger because too small a pulse width results in too large a spectral bandwidth and a reduction occurs in a spectral resolution. The pulse width herein is a half band width of the pulse light.

As described above, a pulse light emitted from the light source has a pulse width selected from a range of 1 ps to 1 ns.

Further, each of the pulse lights emitted from the light source according to the embodiment preferably has a center wavelength in a range of 300 nm to 1500 nm, and particularly preferably in a range of 700 nm to 1300 nm.

The light source preferably has a pulse rate of 1 MHz to 1 GHz.

In the meanwhile, as the multiplexer for multiplexing a plurality of pulse lights with different center wavelengths, an optical coupler, diffraction gratings, prism, etc. may be used.

Subsequently, the information acquiring section will be described. The information acquiring section 108 according to the embodiment acquires information on the object 105 based on the time waveforms of the intensities of lights detected by the optical detecting sections 106 and 107.

The information acquiring section 108 may be configured, for example, to include a CPU-equipped computer storing an application with a synchronization detecting function.

Alternatively, the information acquiring section 108 may be configured to include a unit with a synchronization detecting function, such as a lock-in amplifier (lock-in detecting section). Since a Raman scattering cross section σ of a molecule is generally small, a change in the intensity of a pump light or a Stokes light generated due to stimulated Raman scattering is also a minor one.

For this reason, when a SRS signal is detected from the change in the intensity of the pump light or the Stokes light, the signal is sometimes buried in a noise component, for example, of the pump light.

Therefore, it is preferable that one of the pump light and the Stokes light is allowed to have an intensity modulated by a certain frequency and synchronization detection is performed on a SRS signal changing in synchronization with the frequency.

In this way, highly sensitive detection of a SRS signal is enabled by amplifying a signal synchronization-detected.

Note that a FFT analyzer may be used instead of a lock-in amplifier. Using a FFT analyzer provides more rapid detection of a SRS signal than using a lock-in amplifier.

EMBODIMENT

Exemplary embodiments of the present invention will be hereinafter described.

First Embodiment

Figure 4:
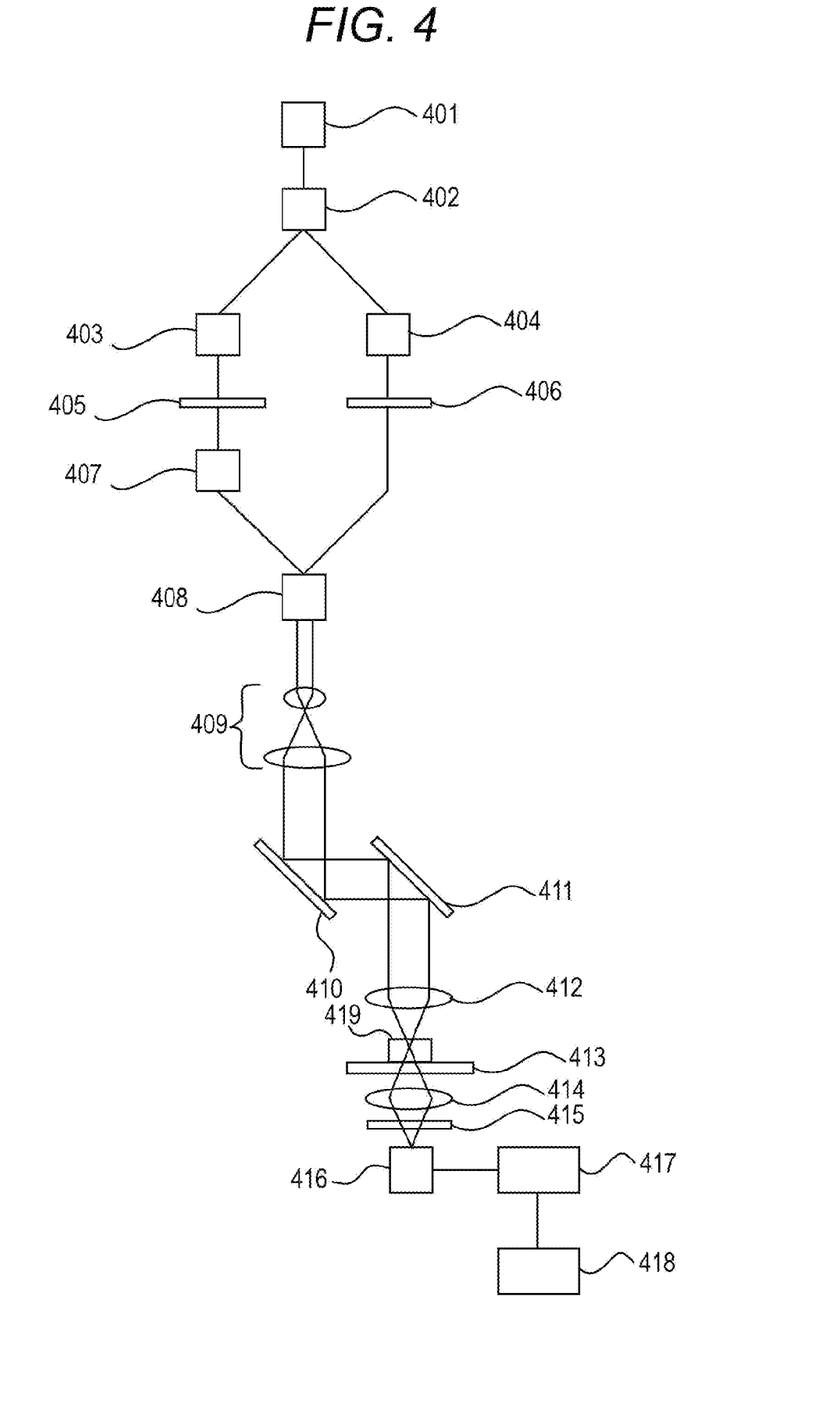
FIG. 4 is a schematic drawing illustrating an exemplary configuration of a stimulated Raman spectroscopy microscope device according to a first embodiment.

Descriptions will be made with reference to FIG. of a first embodiment, which is an example of a configuration of a stimulated Raman spectroscopy (SRS) microscope device using a wavelength variable pulse laser according to the present invention.

The stimulated Raman spectroscopy microscope device according to this embodiment includes a pulse laser 401 configured to emit pulsed light with a variable center wavelength, an optical divider 402, waveguides 403 and 404, band-pass filters 405 and 406, an optical modulator 407, an optical multiplexer 408, and a beam expander 409.

The stimulated Raman spectroscopy microscope device according to the embodiment further includes an X-scan mirror 410, a Y-scan mirror 411, an objective lens 412, a stage 413, a light collecting lens 414, a band-pass filter 415, a light receiving element 416, a synchronization detector 417, and a control unit 418.

On the stage 413, an observation object (measurement object) 419 is arranged. As the object 419, a biological tissue sample is used.

As the pulse laser 401, a mode-locked ytterbium (Yb)-doped fiber laser is used. The laser has a laser resonator storing a wavelength filter, which can vary the wavelength in the gain bandwidth of Yb.

For the pulse laser 401, the wavelength variable range is 1020 nm to 1040 nm, the spectral bandwidth is 0.1 nm, the pulse width is 10 ps, the peak power is 1 kW, and the repetition frequency of the pulse is 100 MHz.

A light output from the pulse laser 401 is divided into two light beams by the optical divider 402. The two light beams follow different optical paths and are guided into the two waveguides 403 and 404, respectively.

As the waveguide 403, a photonic crystal fiber with a zero dispersion wavelength of 1050 nm is used.

As the waveguide 404, a photonic crystal fiber with a zero dispersion wavelength of 1080 nm is used.

Further, the photonic crystal fibers as the waveguides 403 and 404 have a group velocity dispersion β2 of which primary derivative β3 is 1E−40 ($s^3$/m) and secondary derivative β4 is −5E−55 ($s^4$/m), a non-linear coefficient γ of 0.01 (1/W/km), and a fiber length of 1 m.

A light output from the pulse laser 401 is divided into two lights and converted in wavelength by the two waveguides 403 and 404, respectively. When the wavelength of the pulse laser 401 is set at 1020 nm, the waveguide 403 generates conversion lights with two wavelengths of 850 nm and 1270 nm and the waveguide 404 generates conversion lights with two wavelengths of 800 nm and 1400 nm.

Further, when the wavelength of the pulse laser 401 is varied in a range of 1020 nm to 1040 nm, the waveguide 403 generates a conversion light with a wavelength changeable in ranges of 850 nm to 920 nm and 1190 nm to 1270 nm.

Moreover, the waveguide 404 generates a conversion light with a wavelength changeable in ranges of 800 nm to 850 nm and 1300 nm to 1400 nm.

The above conversion lights have a spectral bandwidth of approximately 0.1 nm. The wavelength variable range and the spectral bandwidth are nearly equal to values obtained by substituting the above values into Formula (1) and Formula (2).

Lights output from the waveguides 403 and 404 pass through the band-pass filters 405 and 406, respectively.

The band-pass filter 405 is set so that lights with wavelengths of 850 nm to 920 nm can pass through and the other lights cannot pass through, and the band-pass filter 406 is set so that lights with wavelengths of 800 nm to 850 nm can pass through and the other lights cannot pass through.

A light output from the band-pass filter 405 and a light output from the band-pass filter 406 are used as a Stokes light and a pump light of stimulated Raman scattering, respectively.

The optical modulator 407 modulates the intensity of a light output from the band-pass filter 405 with a modulation frequency of 10 MHz.

Lights output from the band-pass filter 406 and the optical modulator 407 are multiplexed by the optical multiplexer 408 and are converted into a light flux with a large diameter by the beam expander 409.

Although the embodiment uses an optical coupler as the optical multiplexer 408, diffraction gratings or prism may be used.

The output light passes through the X-scan mirror 410 and the Y-scan mirror 411 and is collected to the object 419 on the stage 413 by the objective lens 412.

On a micro region of the object 419 at the center of the light collecting point for the objective lens 412, stimulated Raman scattering generates based on molecular vibration of molecules, whereby a change occurs in the intensities of the Stokes light and the pump light.

Stimulated Raman scattering does not generate in regions away from the micro region at the center of the light collecting point, and no change thus occurs in the intensities of the Stokes light and the pump light.

The laser spot has a smaller size as the objective lens 412 has a larger NA, and the micro region where stimulated Raman scattering generates becomes narrower accordingly.

The pump light of which intensity has been varied due to stimulated Raman scattering generated in the micro region at the center of the light collecting point passes through the objective lens 412, and then passes through the light collecting lens 414 and the band-pass filter 415, and finally enters the light receiving element 416.

The band-pass filter 415 prevents unnecessary lights from entering the light receiving element 416. Since the pump light is 800 nm to 850 nm in wavelength, the band-pass filter 415 is set so that lights with wavelengths of 800 nm to 850 nm can pass through and the other lights cannot pass through.

Further, a pair of galvanometer mirrors are used as the X-scan mirror 410 and the Y-scan mirror 411. The X-scan mirror 410 is for main scanning and the Y-scan mirror 411 is for sub scanning. The mirrors 410 and 411 are arranged so that the rotation axes thereof are perpendicular to each other, and are driven by the control unit 418.

When the X-scan mirror 410 is driven, the light collecting point is scanned in an X-direction within the object 419.

On the other hand, when the Y-scan mirror 411 is driven, the light collecting point is scanned in a Y-direction within the object 419, the Y-direction being perpendicular to the X-direction.

Note that the X-direction and Y-direction are set to be perpendicular to the direction of the optical axis of the objective lens 412. Therefore, the inside of the object 419 can be scanned two-dimensionally with the light collecting point if the angle of the Y-scan mirror 411 is changed by one pitch every time the angle of the X-scan mirror 410 is reciprocated one time.

Subsequently, after a single two-dimensional scanning, the stage 413 is moved to shift the light collecting point by a predetermined distance in the direction of the optical axis and two-dimensional scanning similar to the above scanning is repeated, so that a three-dimensional image of the object 419 can be obtained.

A signal detected by the light receiving element 416 is input to the synchronization detector 417.

A signal component of 10 MHz is measured using a lock-in amplifier as the synchronization detector 417. Note that a FFT analyzer may be used as the synchronization detector 417 although the embodiment employs a lock-in amplifier.

Generating a plurality of wavelength-converted lights with different center wavelengths, using two waveguides 403 and 404 with different zero dispersion wavelengths, as described above makes it possible to expand the wavelength variable range of the pulse light.

In addition, since the wavelength-converted lights have small amounts of noise components, an excellent signal-to-noise ratio can be realized by using the wavelength-converted lights alone for information acquisition.

Moreover, the two photonic crystal fibers configured so as to output shorter-wavelength lights achieves a reduction in the difference between the two wavelengths.

Hence, the configuration of the first embodiment is advantageous for measuring a low Raman frequency.

Second Embodiment

Figure 5:
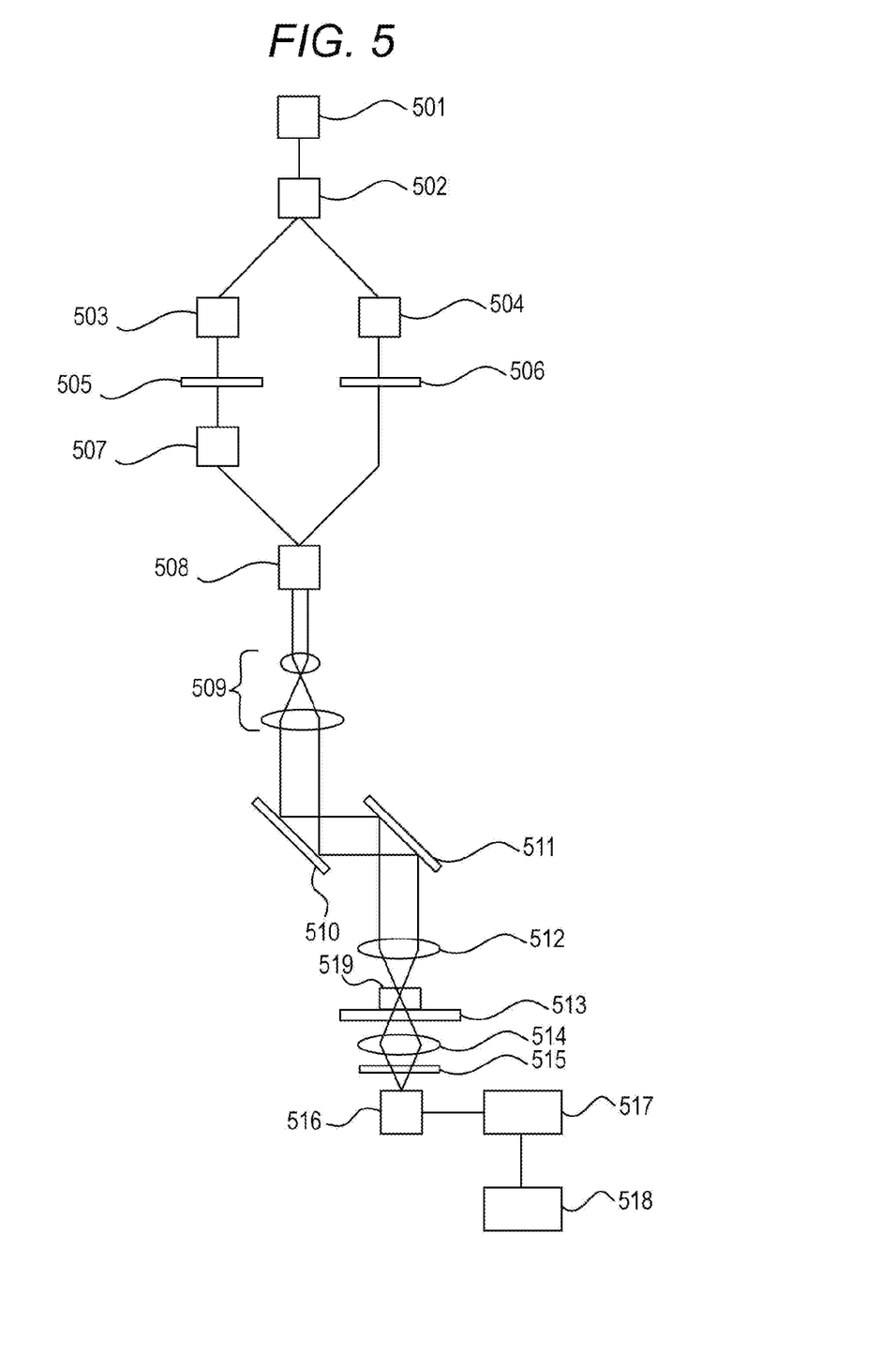
FIG. 5 is a schematic drawing illustrating an example of a configuration of a stimulated Raman spectroscopy microscope device according to a second embodiment.

Descriptions will be made with reference to FIG. 5 of a second embodiment, which is an example of a configuration of a stimulated Raman spectroscopy microscope device using a wavelength variable pulse laser formed differently from that according to the first embodiment.

The stimulated Raman spectroscopy microscope device according to this embodiment includes a pulse laser 501 with a variable center wavelength, an optical divider 502, waveguides 503 and 504, band-pass filters 505 and 506, an optical modulator 507, an optical multiplexer 508, and a beam expander 509.

The stimulated Raman spectroscopy microscope device according to the embodiment further includes an X-scan mirror 510, a Y-scan mirror 511, an objective lens 512, a stage 513, a light collecting lens 514, a band-pass filter 515, a light receiving element 516, a synchronization detector 517, and a control unit 518.

The device according to the second embodiment is similar to that according to the first embodiment except for the configurations of the band-pass filters 505 and 506.

On the stage 513, an observation object (measurement object) 519 is arranged. As the object 519, a biological tissue sample is used.

As the pulse laser 501, a mode-locked ytterbium (Yb)-doped fiber laser is used. The laser has a laser resonator storing a wavelength filter, which can vary the wavelength in the gain bandwidth of Yb.

For the pulse laser 501, the wavelength variable range is 1020 nm to 1040 nm, the spectral bandwidth is 0.1 nm, the pulse width is 10 ps, the peak power is 1 kW, and the repetition frequency of the pulse is 100 MHz.

A light output from the pulse laser 501 is divided into two lights by the optical divider 502 and is emitted into the two waveguides 503 and 504, respectively. As the waveguide 503, a photonic crystal fiber with a zero dispersion wavelength of 1050 nm is used.

As the waveguide 504, a photonic crystal fiber with a zero dispersion wavelength of 1080 nm is used.

Further, the photonic crystal fibers as the waveguides 503 and 504 have a group velocity dispersion $\beta 2$ of which primary derivative $\beta 3$ is $1E-40$ $(s^3/m)$ and secondary derivative $\beta 4$ is $-5E-55$ $(s^4/m)$, a non-linear coefficient $\gamma$ of 0.01 (1/W/km), and a fiber length of 1 m.

A light output from the pulse laser 501 is divided into two lights and is converted in wavelength by the two waveguides 503 and 504, respectively. When the wavelength of the pulse laser 501 is set at 1020 nm, the waveguide 503 generates conversion lights with two wavelengths of 850 nm and 1270 nm and the waveguide 504 generates conversion lights with two wavelengths of 800 nm and 1400 nm.

Further, when the wavelength of the pulse laser 501 is varied in a range of 1020 nm to 1040 nm, the waveguide 503 generates a conversion light with a wavelength changeable in ranges of 850 nm to 920 nm and 1190 nm to 1270 nm.

Moreover, the waveguide 504 generates a conversion light with a wavelength changeable in ranges of 800 nm to 850 nm and 1300 nm to 1400 nm. The above conversion lights have a spectral bandwidth of approximately 0.1 nm. The wavelength variable range and the spectral bandwidth are nearly equal to values obtained by substituting the above values into Formula (1) and Formula (2).

Lights output from the waveguides 503 and 504 pass through the band-pass filters 505 and 506, respectively.

The band-pass filter 505 is set so that lights with wavelengths of 1190 nm to 1270 nm can pass through and the other lights cannot pass through, and the band-pass filter 506 is set so that lights with wavelengths of 800 nm to 850 nm can pass through and the other lights cannot pass through.

A light output from the band-pass filter 505 and a light output from the band-pass filter 506 are used as a Stokes light and a pump light of stimulated Raman scattering, respectively.

The optical modulator 507 modulates the intensity of a light output from the band-pass filter 505 with a modulation frequency of 10 MHz.

Lights output from the band-pass filter 506 and the optical modulator 507 are multiplexed by the optical multiplexer 508 and are converted into a light flux with a large diameter by the beam expander 509.

Although the embodiment uses an optical coupler as the optical multiplexer 508, diffraction gratings or prism may be used.

The output light passes through the X-scan mirror 510 and the Y-scan mirror 511 and is collected to the object 519 on the stage 513 by the objective lens 512.

On a micro region of the object 519 at the center of the light collecting point for the objective lens 512, stimulated Raman scattering generates based on molecular vibration of molecules, whereby a change occurs in the intensities of the Stokes light and the pump light.

Stimulated Raman scattering does not generate in regions away from the micro region at the center of the light collecting point, and no change thus occurs in the intensities of the Stokes light and the pump light. The laser spot has a smaller size as the objective lens 512 has a larger NA, and the micro region where stimulated Raman scattering generates becomes narrower accordingly.

The pump light of which intensity has been varied due to stimulated Raman scattering generated in the micro region at the center of the light collecting point passes through the objective lens 512, and then passes through the light collecting lens 514 and the band-pass filter 515, and finally enters the light receiving element 516.

The band-pass filter 515 prevents unnecessary lights from entering the light receiving element 516. Since the pump light has a wavelength of 800 nm to 850 nm, the band-pass filter 515 is set so that lights with wavelengths of 800 nm to 850 nm can pass through and the other lights cannot pass through.

Further, a pair of galvanometer mirrors are used as the X-scan mirror 510 and the Y-scan mirror 511.

The X-scan mirror 510 is for main scanning and the Y-scan mirror 511 is for sub scanning. The mirrors 510 and 511 are arranged so that the rotation axes thereof are perpendicular to each other, and are driven by the control unit 518.

When the X-scan mirror 510 is driven, the light collecting point is scanned in an X-direction within the object 519.

On the other hand, when the Y-scan mirror 511 is driven, the light collecting point is scanned in a Y-direction within the object 519, the Y-direction being perpendicular to the X-direction.

Note that the X-direction and Y-direction are set to be perpendicular to the direction of the optical axis of the objective lens 512.

Therefore, the inside of the object 519 can be scanned two-dimensionally with the light collecting point if the angle of the Y-scan mirror 511 is changed by one pitch every time the angle of the X-scan mirror 510 is reciprocated one time.

Subsequently, after a single two-dimensional scanning, the stage 513 is moved to shift the light collecting point by a predetermined distance in the direction of the optical axis and two-dimensional scanning similar to the above scanning is repeated, so that a three-dimensional image of the object 519 can be obtained.

A signal detected by the light receiving element 516 is input to the synchronization detector 517. A signal component of 10 MHz is measured using a lock-in amplifier as the synchronization detector 517.

Note that a FFT analyzer may be used as the synchronization detector 517 although the embodiment employs a lock-in amplifier.

Generating a plurality of wavelength-converted lights with different center wavelengths, using two waveguides 503 and 504 with different zero dispersion wavelengths, as described above makes it possible to extend the wavelength variable range of the pulse light.

In addition, since the wavelength-converted lights have small amounts of noise components, an excellent signal-to-noise ratio can be realized by using the wavelength-converted lights alone for information acquisition.

Moreover, the two photonic crystal fibers configured so that one of them outputs a shorter-wavelength light and the other outputs a longer-wavelength light achieves an increase in the difference between the two wavelengths.

Hence, the configuration of the second embodiment is advantageous for measuring a high Raman frequency.

The present invention can provide an information acquiring device that uses pulse lights with high efficiency and with wavelengths variable in a wider range.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-163364, filed Aug. 6, 2013, which is hereby incorporated by reference herein in its entirety.

What is claimed is:

1. An information acquiring device that acquires information of an object, comprising:
    a light source configured to emit pulsed light having a center wavelength $\lambda c$;
    a dividing section configured to divide the pulsed light having center wavelength $\lambda c$ into lights for a plurality of optical paths;
    a plurality of waveguides each provided in each of the optical paths, wherein each waveguide is configured to receive from the dividing section a pulsed light having the center wavelength $\lambda c$ and output a pulsed light having a center wavelength different from the center wavelength $\lambda c$;
    a multiplexing section configured to multiplex lights output from the waveguides;
    an optical system configured to irradiate the object with the lights multiplexed by the multiplexing section; and
    an information acquiring section configured to acquire information of the object through detection of a light generated by applying the lights multiplexed by the multiplexing section to the object, wherein
    each of the waveguides provided in each of the optical paths has different zero dispersion wavelengths,
    each of the waveguides provided in each of the optical paths converts the pulsed light which is divided by the dividing section and has the center wavelength $\lambda c$ into light having a center wavelength different from the center wavelength $\lambda c$, by a nonlinear effect on the waveguide, and
    each of the waveguides satisfies $\beta 2>0$ and $\beta 4<0$ at the center wavelength $\lambda c$, where $\beta 2$ is group velocity dispersion for the waveguides and $\beta 4$ is a second derivative of the group velocity dispersion $\beta 2$.

2. The information acquiring device according to claim 1, wherein the object is irradiated with the wavelength-converted lights alone emitted from the waveguides, and each of the wavelength-converted lights having a center wavelength different from the center wavelength of $\lambda c$.

3. The information acquiring device according to claim 1, wherein the light source includes a pulse laser configured to emit light with a variable center wavelength.

4. The information acquiring device according to claim 1, wherein the light source emits pulsed light with a pulse width ranging from 1 ps to 1 ns.

5. The information acquiring device according to claim 1, wherein the light source has a pulse repetition rate ranging from 1 MHz to 1 GHz.

6. The information acquiring device according to claim 1, wherein the information acquiring section includes a detecting section that detects light generated by stimulated Raman scattering based on molecular vibration of molecules in the object or light generated by coherent anti-stokes Raman scattering.

7. The information acquiring device according to claim 1, wherein the information acquiring section includes a lock-in detecting section.

8. The information acquiring device according to claim 1, wherein the plurality of waveguides are at least two waveguides and are each configured to output light having a shorter-wavelength than light arriving thereto.

9. The information acquiring device according to claim 1, wherein the plurality of waveguides are at least two waveguides, the two waveguides being configured so that a first waveguide outputs light having a shorter wavelength than light arriving thereto, and a second waveguide outputs light having a longer wavelength than light arriving thereto.

10. The information acquiring device according to claim 1, wherein the information acquiring device is a microscope device.

11. The information acquiring device according to claim 10, wherein the microscope device is a stimulated Raman spectroscopy microscope device.

12. The information acquiring device according to claim 1, further comprising a light detection system configured to detect the light generated by applying the lights multiplexed by the multiplexing section to the object,
    wherein the detection system includes a first detector and a second detector,
    wherein the first detector detects light having passed through the object, and the second detector detects light reflected or scattered by the object.

13. The information acquiring device according to claim 1, wherein each of the waveguides satisfies:

$$\Delta \lambda = \frac{1}{A}\sqrt{\frac{12\beta_2}{|\beta_4|}} = \frac{1}{A}\sqrt{\frac{12\beta_3 A(\lambda_0 - \lambda_c)}{|\beta_4|}} \quad A = \frac{2\pi c}{\lambda_0^2}$$

where $\lambda 0$ denotes the zero dispersion wavelength of the waveguides.

14. An information acquiring device that acquires information of an object, comprising:
    a light source configured to emit pulsed light having a center wavelength $\lambda c$;
    a dividing section configured to divide the pulsed light having the center wavelength $\lambda c$ into lights for a plurality of optical paths;
    a plurality of waveguides each provided in each of the optical paths, wherein each waveguide is configured to receive a pulsed light which is divided by the dividing section and has the center wavelength $\lambda c$ and output a pulsed light having a different center wavelength;
    a multiplexing section configured to multiplex lights output from the waveguides;
    an optical system configured to irradiate the object with the lights multiplexed by the multiplexing section; and
    an information acquiring section configured to acquire information of the object through detection of a light generated by applying the lights multiplexed by the multiplexing section to the object, wherein
    each of the waveguides provided in each of the optical paths has different zero dispersion wavelength, each of the waveguides provided in each of the optical paths converts the pulsed light which is divided by the dividing section and has the center wavelength λc into light having a center wavelength different from the center wavelength λc, by nonlinear effect on the waveguide, and at least one of the waveguides provided in each of the optical paths satisfies β2>0 and β4<0 at the center wavelength λc, where β2 is group velocity dispersion for the waveguides and β4 is a second derivative of the group velocity dispersion β2.

* * * * *